United States Patent [19]

Stimpson et al.

[11] Patent Number: 5,551,416
[45] Date of Patent: Sep. 3, 1996

[54] NEBULISER AND NEBULISER CONTROL SYSTEM

[75] Inventors: Philip G. Stimpson, Welford; Andrew D. Hopkins, Sutton Coldfield, both of United Kingdom

[73] Assignee: Medix Limited, Lutterworth, United Kingdom

[21] Appl. No.: 232,244

[22] PCT Filed: Nov. 12, 1992

[86] PCT No.: PCT/GB92/02098

§ 371 Date: May 10, 1994

§ 102(e) Date: May 10, 1994

[87] PCT Pub. No.: WO93/09881

PCT Pub. Date: May 27, 1993

[30] Foreign Application Priority Data

Nov. 12, 1991 [GB] United Kingdom .................. 9123969

[51] Int. Cl.⁶ ................................................ A61M 11/00
[52] U.S. Cl. ................................ 128/200.16; 128/200.14; 128/203.12
[58] Field of Search ......................... 128/200.14, 200.16, 128/203.12; 239/101.2, 101.1, 238

[56] References Cited

U.S. PATENT DOCUMENTS

| | | | |
|---|---|---|---|
| 3,804,329 | 4/1974 | Martner | 239/4 |
| 3,866,831 | 2/1975 | Denton | 239/4 |
| 3,989,042 | 11/1976 | Mitsui et al. | 128/194 |
| 4,281,484 | 8/1981 | Massa | 451/2 |
| 4,316,580 | 2/1982 | Bodai | 239/466 |
| 4,318,062 | 3/1982 | Mitsui et al. | 331/109 |
| 4,336,509 | 6/1982 | Bernitz | 331/114 |
| 4,703,213 | 10/1987 | Gäsler | 310/316 |
| 4,823,042 | 4/1989 | Coffey et al. | 310/322 |
| 4,939,402 | 7/1990 | Hirayama et al. | 310/316 |
| 4,976,259 | 12/1990 | Higson et al. | 128/200.16 |
| 5,216,338 | 6/1993 | Wilson | 310/316 |

FOREIGN PATENT DOCUMENTS

| | | | |
|---|---|---|---|
| 0084458 | 7/1983 | European Pat. Off. | F23D 11/34 |
| 0123277 | 10/1984 | European Pat. Off. | B06B 1/06 |
| 0174862 | 3/1986 | European Pat. Off. | B05B 17/06 |
| 0217518 | 4/1987 | European Pat. Off. | B05B 17/06 |
| 0258637 | 3/1988 | European Pat. Off. | B05B 17/06 |
| 0283029 | 9/1988 | European Pat. Off. | B05B 17/06 |
| 3625461 | 4/1988 | Germany | B06B 1/06 |
| 156955 | 1/1988 | Japan . | |
| 2024048 | 1/1980 | United Kingdom | B05B 17/06 |
| 2101500 | 1/1983 | United Kingdom | B05B 17/06 |
| 2107611 | 5/1983 | United Kingdom | B05B 17/06 |
| 2126923 | 4/1984 | United Kingdom | B05B 17/06 |
| 2224446 | 5/1990 | United Kingdom | A16H 11/00 |

OTHER PUBLICATIONS

Patent Abstracts of Japan, vol. 4, No. 180 12, Dec. 1980.
Patent Abstracts of Japan, vol. 12, No. 221 23, Jun. 1988.

*Primary Examiner*—Edgar S. Burr
*Assistant Examiner*—William J. Deane, Jr.
*Attorney, Agent, or Firm*—Michael G. Johnston; Richard W. Evans; Moore & Van Allen PLLC

[57] ABSTRACT

A nebulizer for use in administering a medicament to a patient undergoing treatment for example, comprises an ultrasonic piezo-electric transducer (60) and a transducer drive system (D) which is caused to drive said transducer at or near its anti-resonant frequency. There is also provided means to optimize nebulized fluid particle size and transfer to the patients lungs for example, by operating at an anti-resonant frequency in the range of 1.36 to 1.56 MHz and having a single outlet baffle and relatively short outlet tube (24) arrangement.

8 Claims, 11 Drawing Sheets

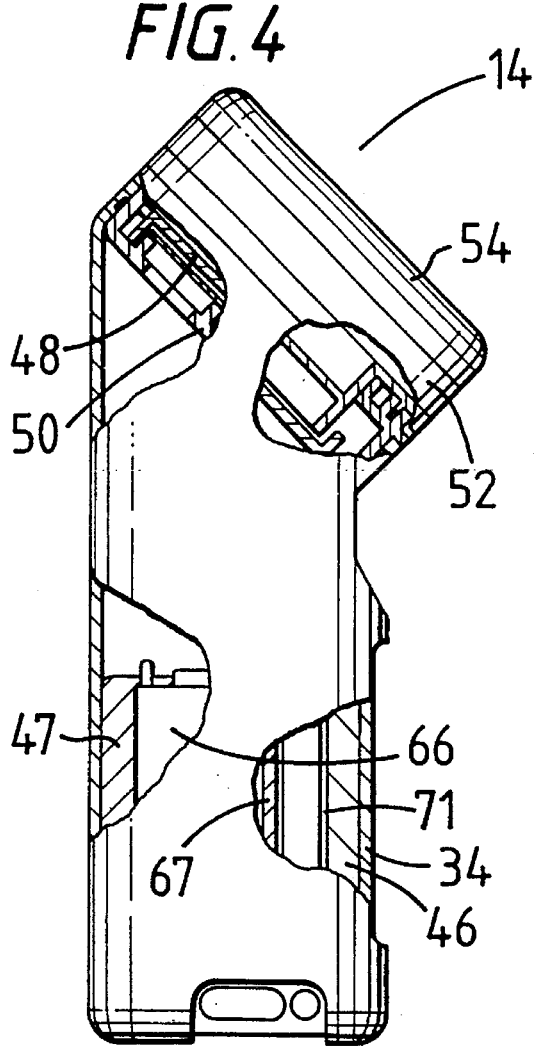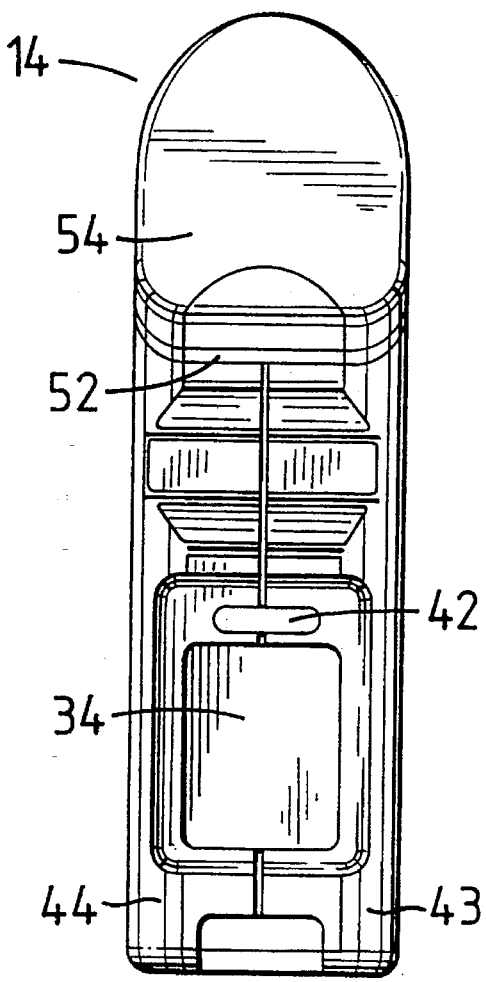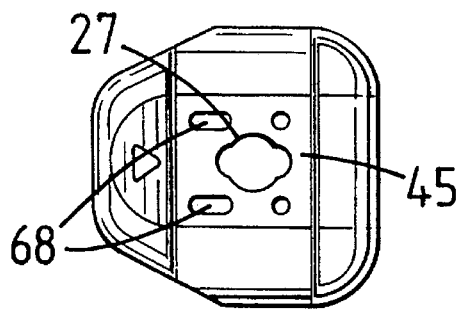

NEBULISER AND NEBULISER CONTROL SYSTEM

The invention relates to a nebuliser such as an ultrasonic device used to generate a fine mist of therapeutic fluid which can be inhaled by a patient undergoing treatment. The invention further relates to a control system for optimising preset characteristics of the nebuliser.

It is known to produce a nebulised medicament using an ultrasonic transducer which may be an electrically driven piezo-electric crystal. The transducer produces a mechanical vibration which is transferred to a liquid body of medicament. Typically, the vibration may be in the ultrasonic range of the order of 1–2 megahertz. This vibration can cause cavitation, or violent motion, at the liquid surface and thereby generates a mist. It is known that an optimum mist particle size for efficient transfer of the drug to a patients lungs is of the order of 1 to 6 micrometers. It is also known that such nebulisers, or mist creators, have a variety of applications such as distributing cleaning agents in otherwise inaccessible locations and for facial massage or similar cosmetic/dermatological treatments. Also, whilst the words medicament and therapeutic drug are used it is to be understood that water can be inhaled in treatment of health disorders and is therefore included in the meaning of these words.

Several known techniques of nebulising a liquid are disclosed in U.S. Pat. No. 3,387,607 (Gauthier) which uses a transfer fluid to relay the ultrasonic vibration from the transducer to the drug. Gauthier teaches of a technique of focusing the ultrasonic compressional wave to optimise the density of mist created above the liquid body of drug. Density of nebulised fluid is also optimised by Gauthier by setting the transducer drive frequency near, but preferably slightly above its resonant frequency.

A nebuliser control system is disclosed in U.S. Pat. No. 4,319,155 (Omron) which controls the ultrasonic transducer output level using a variable pulse oscillating circuit. Omron varies the output level between two states, effectively "nebulisation on" and "nebulisation off" states, the mark/space ratio of the power signal thereby determines the quantity of nebulised fluid and therefore enables control of the rate of treatment.

A further known nebuliser is disclosed in European patent 174862 (Varian) which uses a method of sweeping through the third harmonic resonant frequency of about 3 MHz compared to the fundamental resonant frequency of about 1 MHz of a piezo-electric crystal. Additionally, the voltage across the crystal is pulsed on and off at a much lower frequency. EP 174862 does not disclose a method of locking onto an operating frequency but rather the crystal is cooled to maintain a constant resonant frequency.

Known devices do not disclose a technique of minimising the current drawn by the transducer drive circuitry. It is not known to drive an ultrasonic transducer at its anti-resonant frequency and optimise nebulisation and drive circuit power consumption in this state. It is not known to periodically scan a range of frequencies and lock onto an anti-resonant frequency thereby to compensate for variation in the anti-resonant frequency of a piezo-electric crystal during operation due, for example, to variation in physical conditions such as temperature. Accordingly, the present invention seeks to avoid or at least mitigate these and other problems of the prior art.

One aspect of the invention provides a nebuliser comprising a piezo-electric crystal transducer which converts an electrical drive signal into mechanical vibration to nebulise a liquid in mechanical contact with said transducer and a transducer drive system which causes said transducer to vibrate at or near its anti-resonant frequency and to maintain vibration at this frequency. The anti-resonant frequency being defined as the crystal frequency characterised by a maximum or elevated electrical impedance.

A feature of this aspect of the invention provides a nebuliser wherein said drive system comprises a nebuliser wherein the drive system comprises:

frequency control means for automatically controlling the frequency of said drive signal such as to maintain energisation of the transducer in said region; and power control means for controlling the power supplied by the drive signal to the transducer in dependence on user input.

A further aspect of the invention provides a nebuliser comprising an electrically-energisable ultrasonic transducer in the form of a piezo-electric crystal, and a transducer drive system for generating a high-frequency drive signal for energising the transducer, the transducer being connected to receive said drive signal and, when energised thereby, being operative to cause physical vibration in a fluid to be nebulised, the transducer drive system including current sensing means for providing a measure of the transducer drive current, and comparator means for comparing said measure with a predetermined threshold value and generating a termination signal indicative of said fluid having been completely nebulised when said measure falls below the threshold value.

Another aspect of the invention provides a nebuliser, a transducer and a transducer drive system which has a step-up transformer comprising primary and secondary coils wherein the secondary coil is connected to said transducer where it is beneficial to match the primary and secondary coils of the transformer at the transducer anti-resonance frequency.

A further aspect provides a nebuliser which comprises a nebulising chamber for holding a fluid in physical contact with the transducer and an air flow passage which passes through said nebulising chamber to draw off nebulised fluid to an outlet, the air flow passage passing through an outlet baffle and an outlet tube.

A further aspect provides a nebuliser comprises a transducer having a piezo-electric crystal comprising two electrical contacts for opposite electrical polarities which crystal also has a shim layer attached to its upper surface and which shim layer is placed in direct contact with the medicament in use.

A further aspect provides a nebuliser comprising a nebulising chamber and a transducer which is placed in a recess in the bottom of the nebulising chamber and held in position using a seal and a clamp means which are placed in contact with said transducer.

Various aspects of the invention will now be described, by way of example only, with reference to the accompanying drawings, in which:

FIG. 4 shows a side elevation drawing of the hand-held nebuliser shown in FIG. 3;

FIG. 5 shows a front elevation view of the hand-held nebuliser unit shown in FIG. 3;

Figure 1:
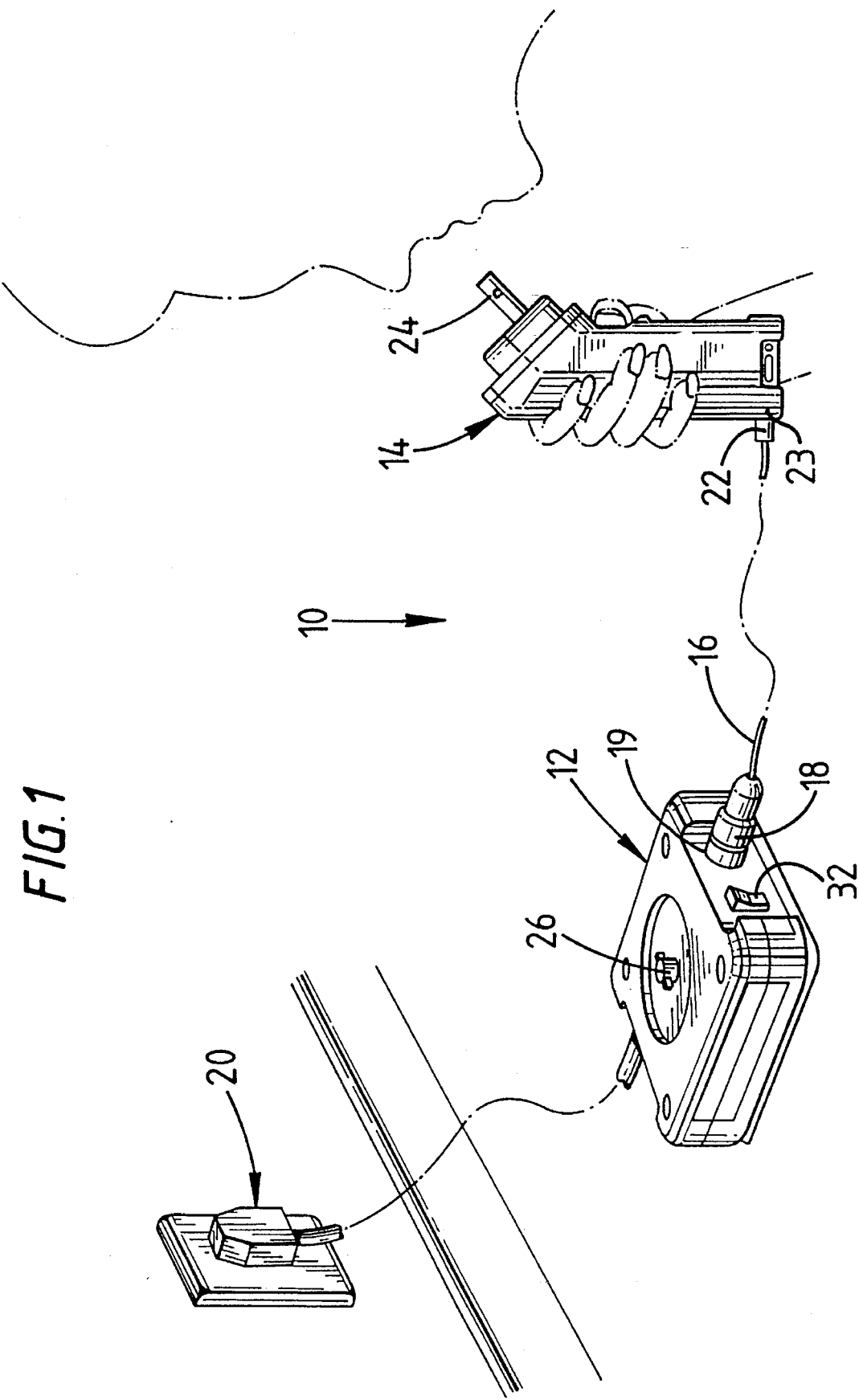
FIG. 1 shows a schematic perspective view of a first embodiment of a nebuliser according to the invention.
Figure 2:
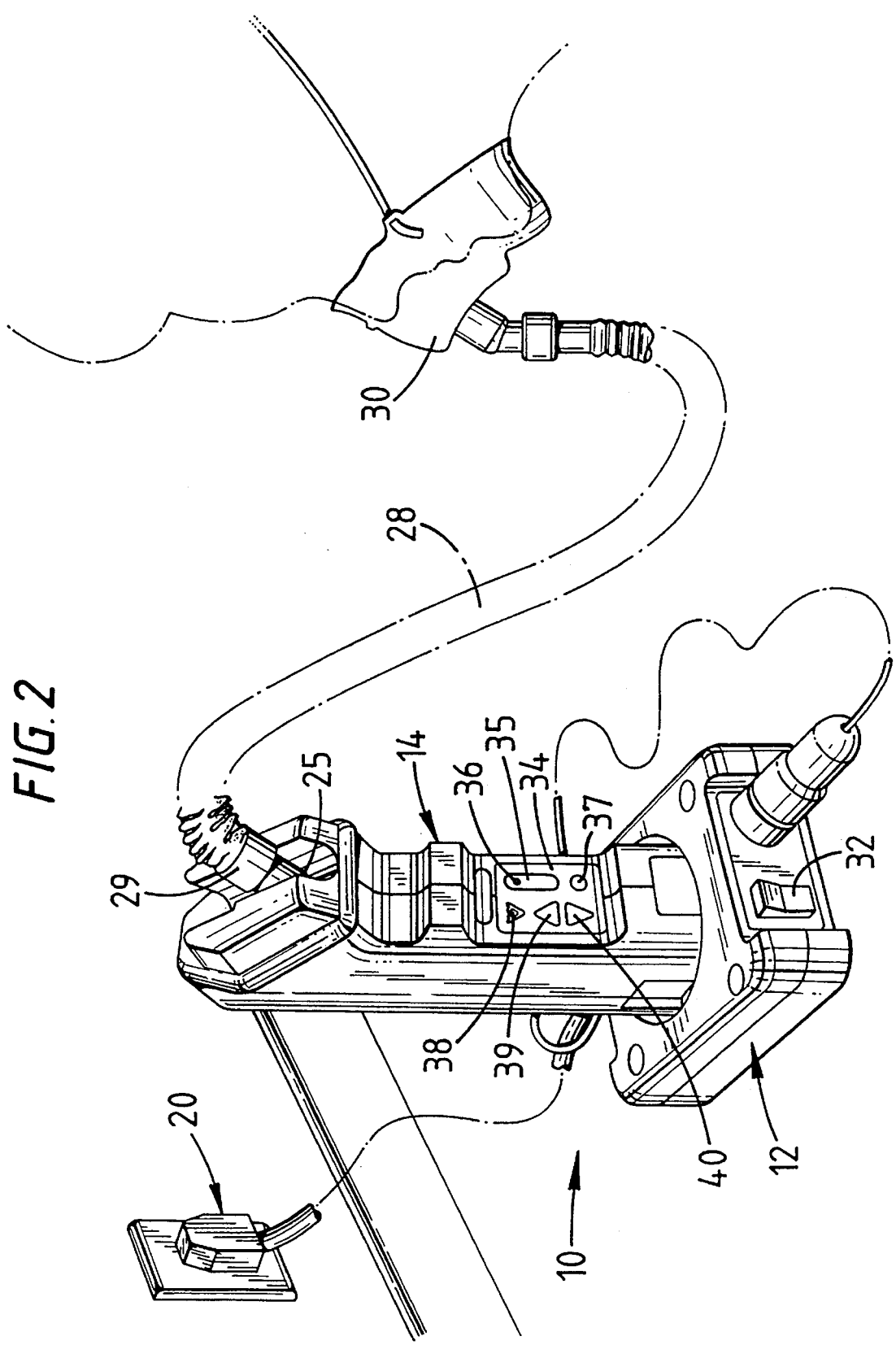
FIG. 2 shows a schematic perspective view of the nebuliser shown in FIG. 1 adapted for use with a face mask.
Figure 3:
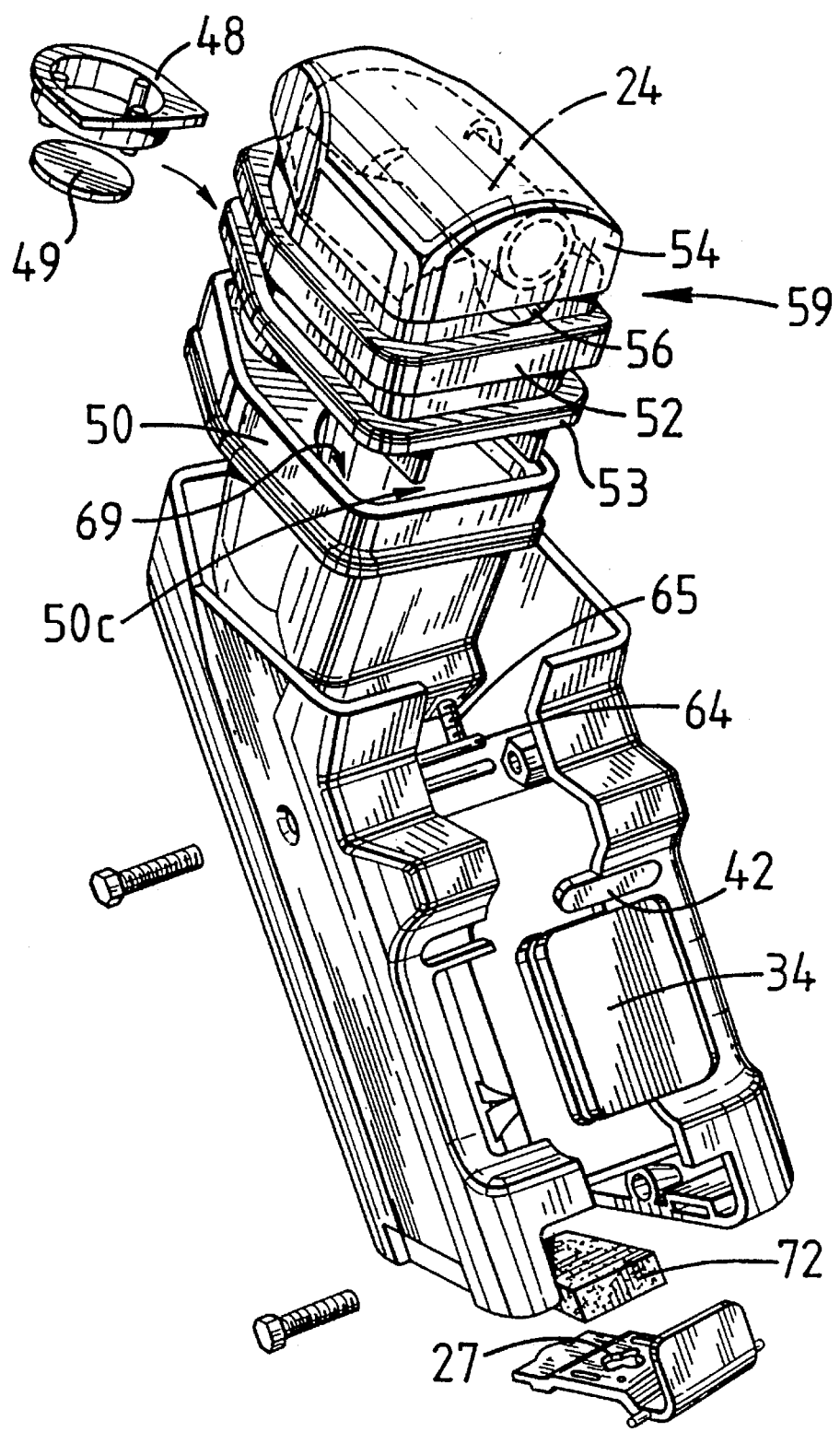
FIG. 3 shows an exploded schematic perspective view of the hand-held unit shown in FIG. 1.
Figure 3A:
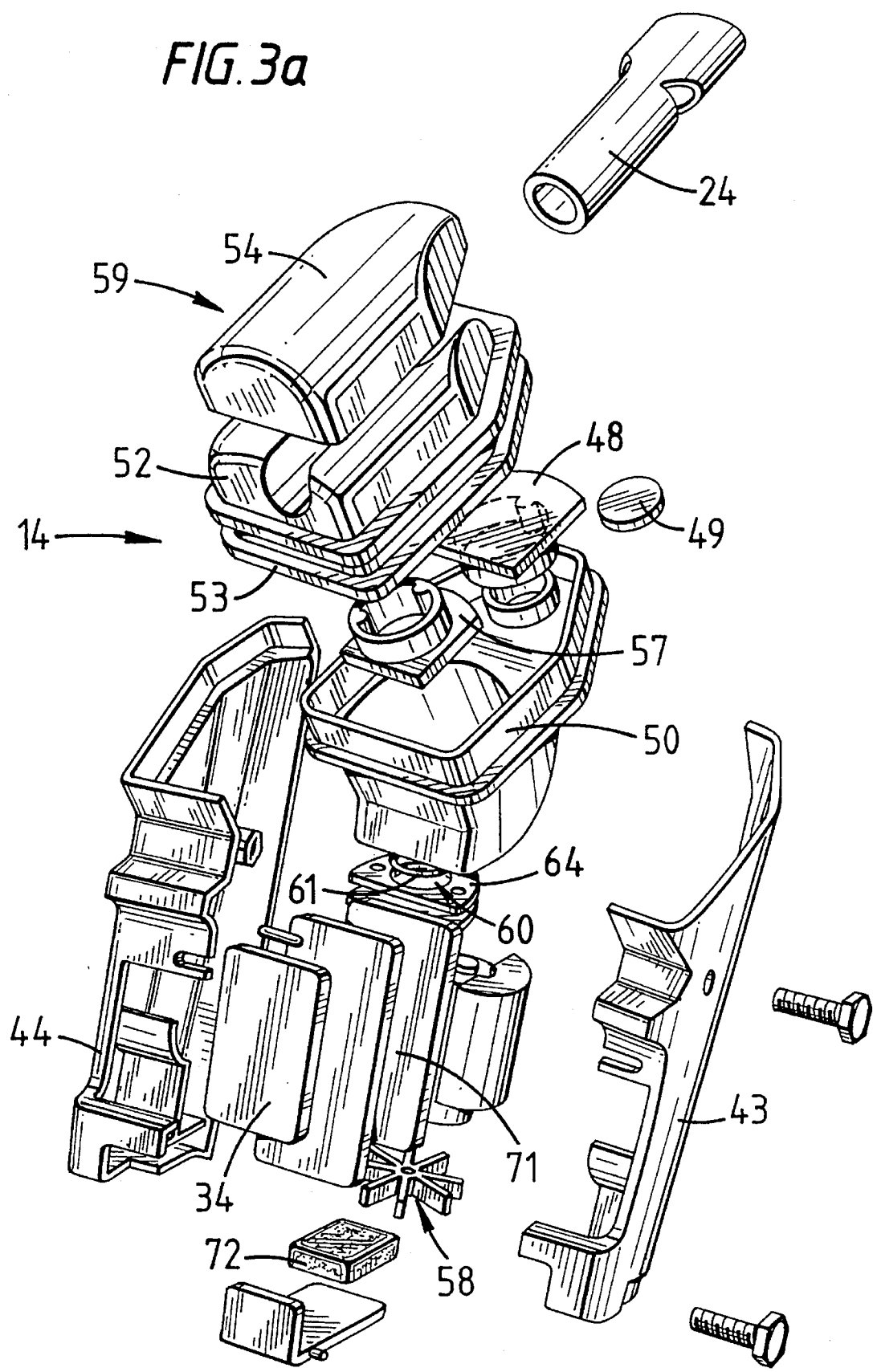
FIG. 3a shows an exploded schematic view of a slightly different hand-held nebuliser to that shown in FIG. 3.

Referring to FIG. 1 there is shown a nebuliser 10 for administering a medicinal drug to a user, or patient, comprising a nebulising unit 14 and power unit 12. This description is directed to use of a nebuliser according to the invention in nebulising a liquid medicament, or drug, for use in therapy. The nebuliser is not limited specifically to this use and could possibly be used with many different fluids or powdered material. Unit 12 comprises a mains voltage transformer and is connected to a mains electricity supply using cable and wall-socket plug 20. Power unit 12 also acts as a base unit to which the hand held nebuliser 14 is mounted when the overall nebuliser system 10 is used in combination with a face mask as shown in FIG. 2 or when storing the device. Unit 12 is relatively heavy and gives stability to the nebuliser 10.

Hand held unit 14 is connected to power unit 12 by electrical cable 16 which comprises connectors 18 and 22. Connector 18 is plugged into socket 19 of power unit 12 whilst connector 22 is plugged into socket 23 of hand-held unit 14.

Connector 18 can also be used to plug hand-held unit 14 into the cigarette lighter socket of a car, for example. Hand-held unit 14 together with cable 16 comprise a portable unit which can be used separately from mains power transformer unit 12. For example, a 12 v dc battery supply could be used to drive the hand-held nebuliser as described later. Unit 12 further comprises a power switch 32 which closes the transformer circuit housed in unit 12 thereby providing power to nebuliser unit 14 via connecting cable 16. Typically in the UK, the transformer unit 12 would step down the mains electricity supply of 240 volts to an output level at socket 19 of 12 volts, for example. Of course, unit 12 could be adapted to suit local mains voltages such as 110 v in the USA. Alternatively, unit 12 may comprise a universal transformer, or switch mode power supply, which is self regulating dependent on the input supply to provide a 12 v dc output. The electrical base unit 12 rectifies the ac input voltage to a dc supply to nebuliser 14. Unit 12 further comprises a catch 26 which acts cooperatively with an aperture 27 provided in the base of unit 14 to lock units 12 and 14 together.

In the view shown in FIG. 1 hand-held unit 14 can be seen to further comprise a mouthpiece 24 through which a user undergoing therapy draws the nebulised medicament. The method of nebulisation and air flow path are described in greater detail with reference to later drawings. It is apparent, however, that a nasal inhalation technique could also be used.

FIG. 2 shows the FIG. 1 nebuliser 10 where hand-held nebulising unit 14 is mounted to power unit 12 in the manner previously described. Instead of using the simple mouthpiece tube 24 shown in FIG. 1, FIG. 2 shows a user wearing a face mask 30 connected to the nebulising unit 14. The face mask is connected using a flexible tube 28 and connector 29 which is inserted in aperture 25 in the top of the nebulising unit 14. In this schematic perspective view of the nebuliser 10 there is also shown control panel 34 which is used by the patient undergoing treatment to control various parameters. Control panel 34 comprises an "on" button 35 which has a light emitting diode (LED) 36 which is turned on when the user begins therapy and remains on until "off" button 37 is depressed or the medicament in the nebulising chamber within nebuliser 14 runs out. The control panel 34 further comprises a liquid level display 38 representative of the medicament in the nebulising chamber. When the medicament liquid has substantially run out a detection means which is described later turns display 38 on and can also provide an audible sound to alert the user to the fact that the drug has run out thus indicating the end of treatment. Indeed, an audible signal can be provided for any of the operations described in relation to control panel 34 which are carried out by the user, for example, a simple beep may be provided when the therapy begins, i.e. when the user presses the "on" button 35. Further controls are provided which increase and decrease the rate of nebulisation of the therapeutic drug using "up" button 39 and "down" button 40. As can be seen in FIG. 2 the "up" and "down" control can be represented symbolically using "up" and "down" arrows.

Hand-held nebuliser unit 14 is shown from various elevations and FIGS. 3, 3a, 4 and 5. Generally, unit 14 comprises two main body portions 43 and 44 into which is fitted the main nebulising chamber unit 50, control panel 34 and top unit 59. Top unit 59 comprises top cover 54, nebulising chamber cover 52 and chamber and baffle cover 53. Top unit 59 as a whole is detachable from hand held nebuliser unit 14 thereby giving access to nebulising chamber 50c which is a cavity defined substantially by nebulising chamber unit 50.

Figures 6, 7:
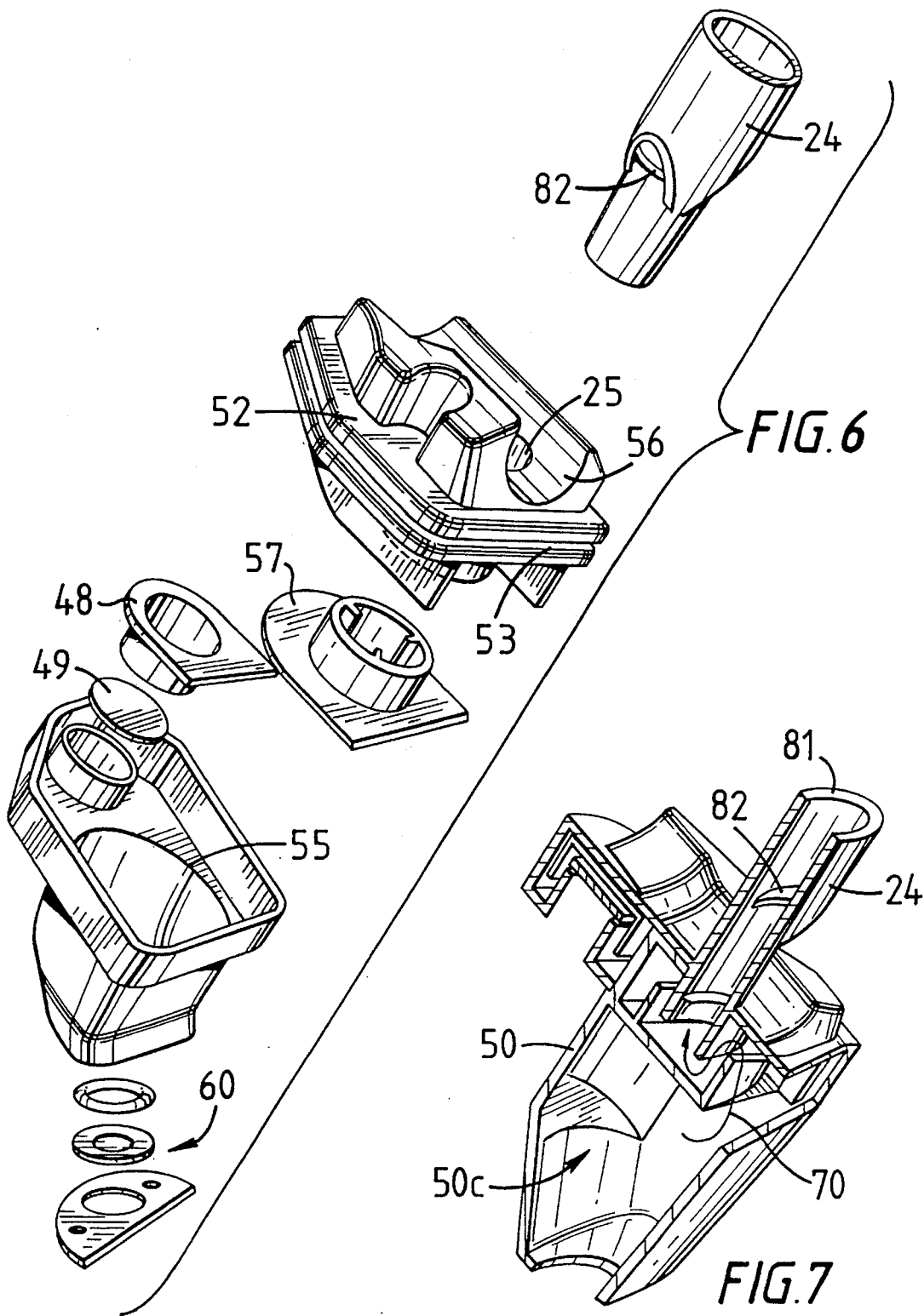
FIG. 6 shows a schematic exploded perspective view of the nebulising chamber and mouthpiece parts of the hand-held nebuliser unit shown in FIG. 3.
FIG. 7 shows a schematic sectional perspective view of the nebulising chamber and mouthpiece shown in FIG. 6.
Figure 7A:
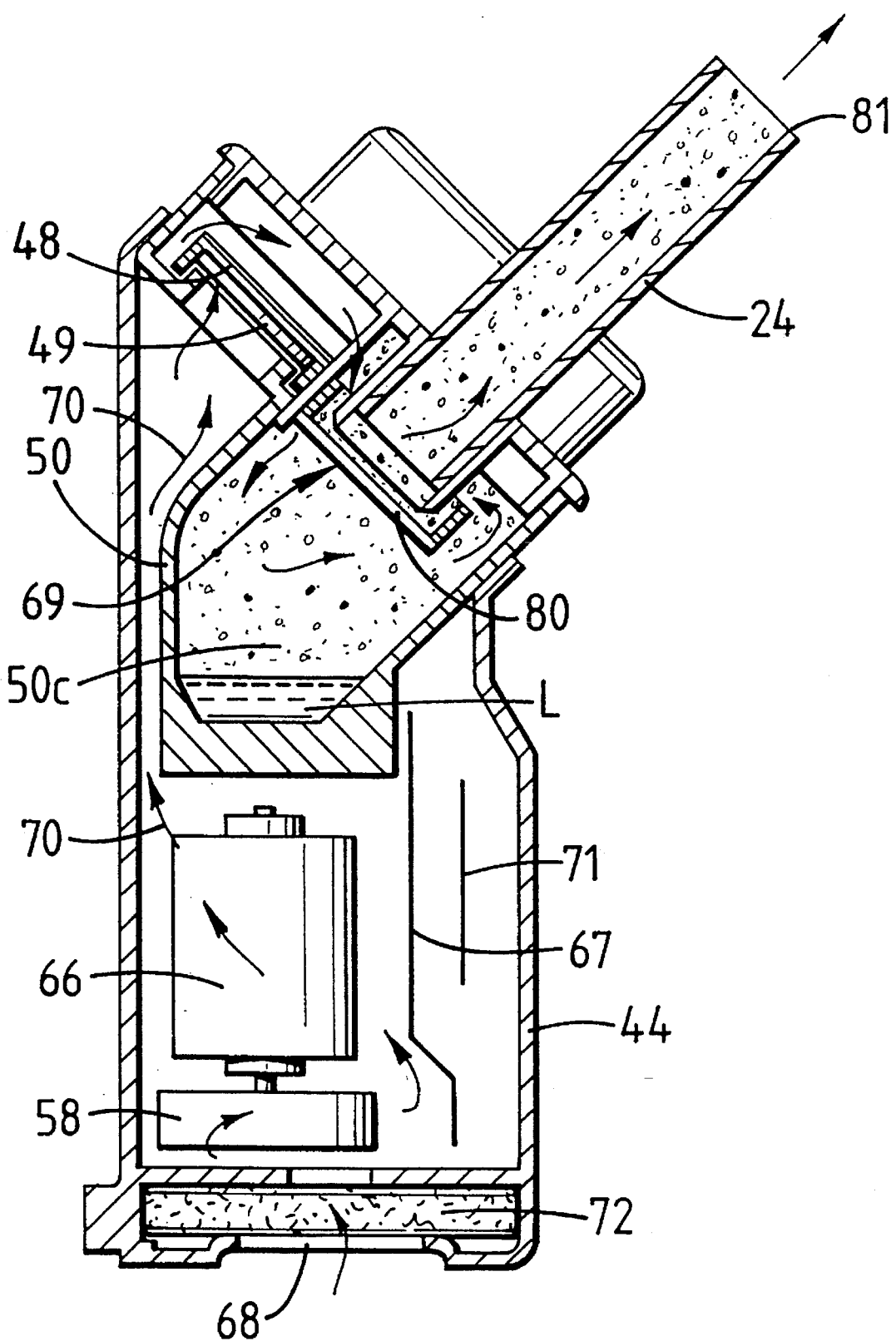
FIG. 7a shows a schematic sectional side elevation of the hand-held nebuliser shown in FIG. 3.

FIGS. 6, 7 and 7a give schematic representations of parts of the nebuliser 14 from which it can be seen how the air flows from an air inlet 68 in the base of unit 14 to the output at mouthpiece 24. Fan 58 is driven by motor 66 and draws air through intakes 68 and filter 72. The filter 72 may, for example, be a light foam material. The air then passes over motor 66 and also acts to cool heat sink 67 which isolates pcb 71 from the air flow path 70.

The air then passes through a non-return valve 49 and is directed by inlet baffle 48, which also acts to retain valve 49 in this embodiment. The air then flows around outlet baffle plate 80 into nebulising chamber 50c through inlet 69. The chamber 50c holds the reservoir of drug L above transducer 60 and is shaped to minimise the surface area above the liquid.

Chamber 50c is therefore designed to be nearly spherical in shape. This minimises condensation and allows any condensed drug to fall back into reservoir L under gravity.

The drug/air mixture is then pumped out through outlet baffle 80 which causes large droplets to be retained by the nebuliser and helps optimise the particle droplet size at the output of mouthpiece 24. Baffle 80 generally acts to cause air flow path 70 to bend through two changes of direction, approximately 180 degrees each. Mouthpiece 24 generally comprises a tube adapted to fit into a user's mouth but could equally be used for nasal inhalation if slightly modified.

Figure 8:
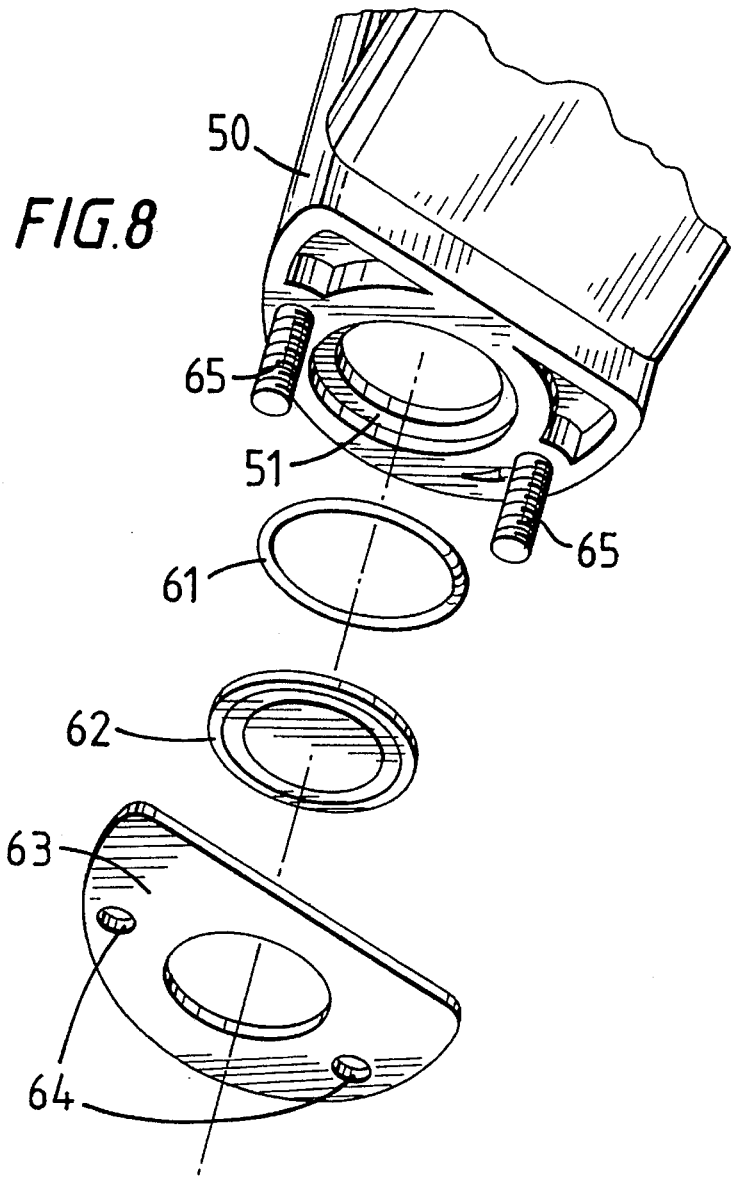
FIG. 8 shows a schematic perspective exploded view of the crystal mounting assembly for the hand held nebulising unit.
Figure 8A:
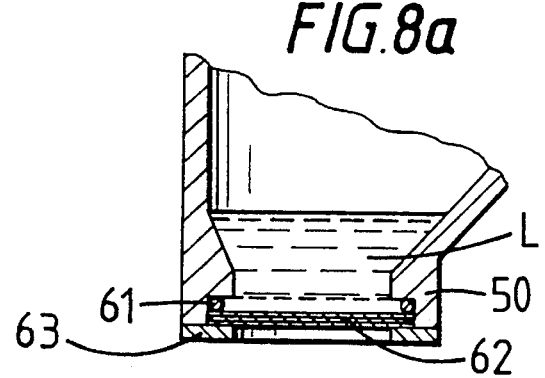
FIG. 8a shows a schematic sectional side elevational view of the completed crystal mounting shown in FIG. 8.

Mouthpiece 24 comprises an outlet 81 and blow-back holes 82. Blow-back holes 82 are designed to allow a user to retain mouthpiece 24 in his or her mouth during therapy; breathing in air containing the drug through outlet 81 and breathing out exhaust gas through outlets 82. It is particularly beneficial that outlets 82 direct the exhaust gases away from the user's face unlike known devices. The hand-held unit 14 comprises a transducer 60 which converts electrical input signals into mechanical vibrations in the ultrasonic frequency range. The transducer 60 comprises a piezo-electric crystal 62. FIGS. 8 and 8*a* show how the crystal is mounted at the bottom of the nebulising chamber unit 50. An o-ring is fitted in recess 51 in the underside of moulded unit 50. The crystal is then inserted in recess 51 and abuts the o-ring such that when the transducer is clamped down there is a good seal at the top surface of the crystal 62 with o-ring 61 and between o-ring 61 and the moulded unit 50 thereby preventing liquid L held in the nebulising chamber 50*c* leaking out. The crystal is clamped in recess 51 using a clamp constituted by heat sink plate 63 which comprises apertures 64 which fit on two bolts 65 suspended from the bottom of nebulising chamber unit 50. The heat sink plate 63 thereby provides a dual purpose in providing sufficient force to retain crystal 62 in recess 51 thereby preventing leakage of liquid L when securely fastened to bolts 65, for example, through the use of fly nuts. It also acts as a relatively large thermal mass with a good thermal conductivity which draws heat quickly away from the crystal. Heat is generated through the mechanical vibration of the crystal and it is important that the crystal does not overheat. A secondary means of preventing overheating is to monitor the temperature using an electrical system described later.

Figure 9:
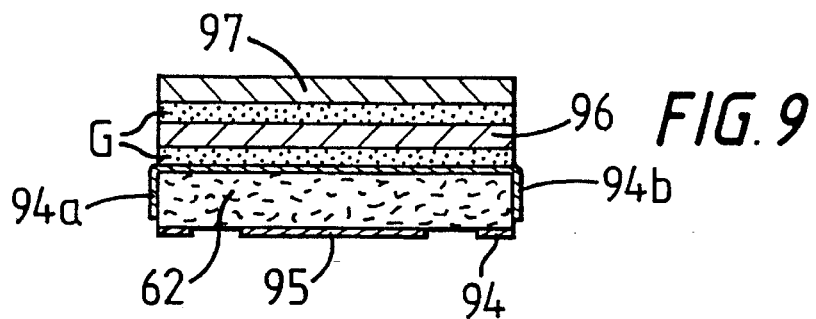
FIG. 9 shows a sectional side elevational view of the piezo electric crystal transducer used in a nebulising unit according to the invention.
Figure 10:
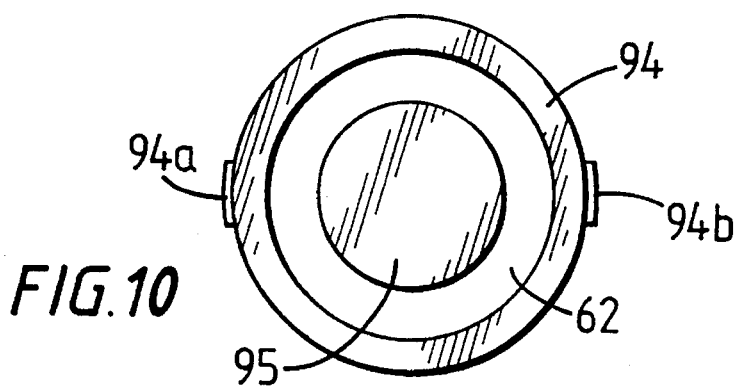
FIG. 10 shows a plan elevation from below of the transducer shown in FIG. 9.

FIGS. 9 and 10 show a side cross-sectional and plan view of the crystal 62 respectively. As an example of a suitable crystal for nebuliser 10 the piezo-electric crystal can be approximately 20 millimeters in diameter and 1.39 millimeters thick. It is coated on one surface with a silver connecting material which is also brought down to two points on the opposite surface at 94*a* and 94*b*. A second electrical connecting point 95 is placed centrally on the lower circular surface of crystal 62 and has a diameter of about 10 millimeters for example. To the top side of crystal 62 a layer of glue is placed above silver connector 94 onto which is placed a layer of aluminium 96 of approximately 0.29 millimeters thickness. This again is coated on its upper side with a layer of glue onto which can be placed 0.1 millimeter layer of stainless steel 97. The upper side of steel layer 97 is in direct contact with liquid L in the bottom of the nebulising chamber 50*c* in use. Alternatively, the transducer crystal above can be made without the layer of aluminium 96. It is also possible to shim crystal 62 with a layer of nickel or a layer of enamel rather than the steel and aluminium combination just described. The properties of the transducer can be varied by changing the shim, for example, the resonant frequency of the transducer described might be 1.6 MHz and 1.45 MHz when unshimmed and when shimmed respectively.

Electrical contacts to the crystal from the drive circuitry described later are made to layer 94 and to layer 95. The contacts can be made using resilient electrical connectors such as thin copper lugs which are capable of remaining in contact with regions 94 and 95 of transducer 60 whilst the crystal vibrates. The crystal itself may, for example, be a compressed barium titanate crystal where the impedance-frequency characteristics (discussed later) can be specified to a manufacturer, together with dimensional requirements for specific nebuliser construction and use.

Figure 11:
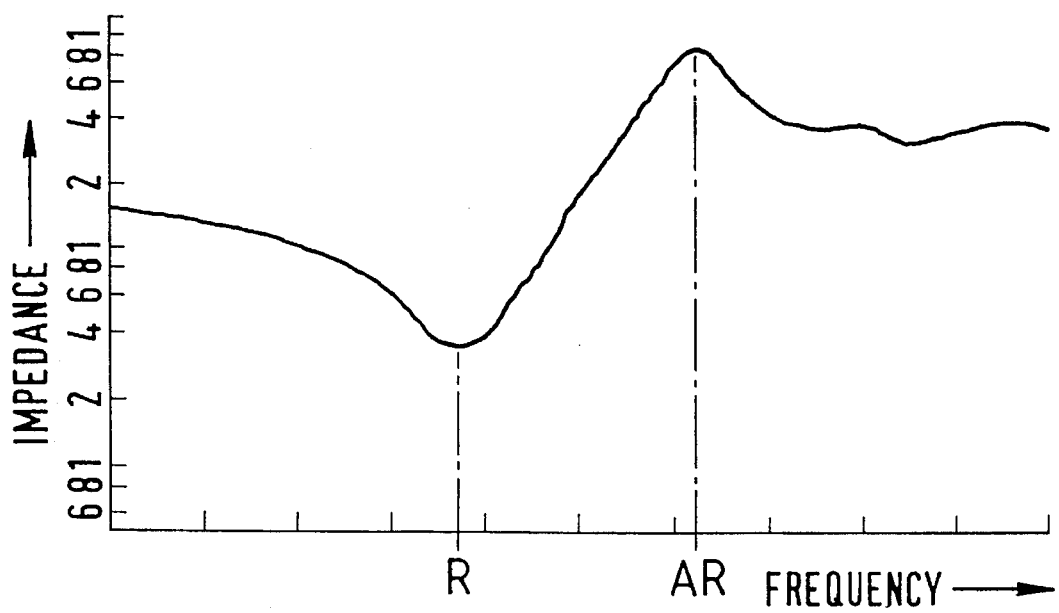
FIG. 11 shows a characteristic impedance versus frequency curve for the transducer crystal.
Figure 12:
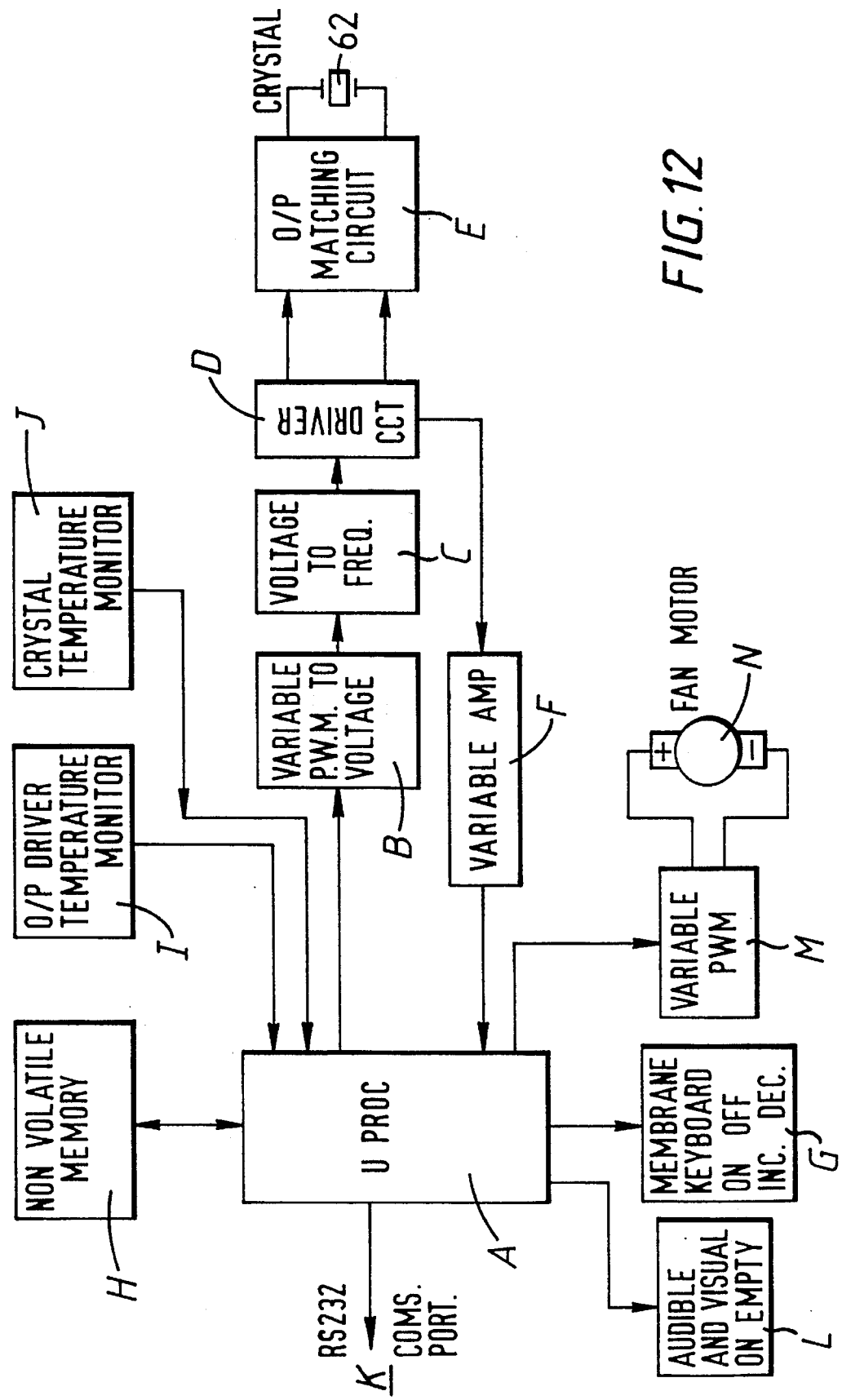
FIG. 12 shows a schematic block diagram of the electronic circuitry used to drive the nebuliser according to the invention.
Figure 13:
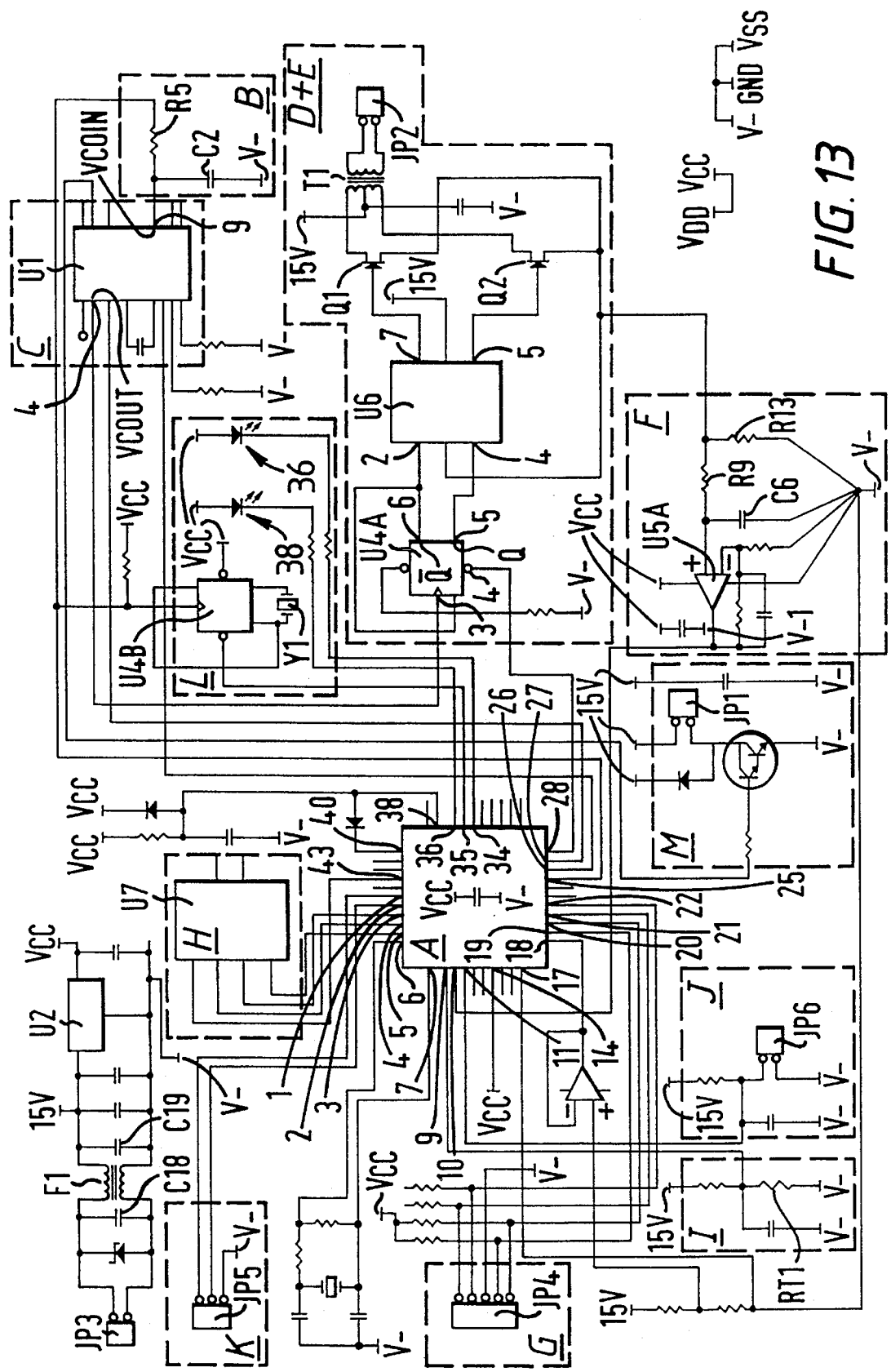
FIG. 13 shows a circuit diagram of the electronics used to drive and control the nebuliser according to the invention.

Electrical circuitry used for controlling and driving the nebuliser is shown in FIGS. 12 and 13, the circuit being housed primarily on printed circuit board 71 housed in nebuliser unit 14. FIG. 12 is a schematic block diagram of the basic elements used to operate the system. Whilst FIG. 13 is an electronics circuit diagram where the components shown in the block diagram 12 are represented schematically by dashed lines. Referring to FIG. 12 it can be seen that the system is substantially controlled by micro-processor A. One of the main aspects of the circuitry is to drive the crystal 62 at its anti-resonant ultrasonic frequency thereby minimising the current drawn by the crystal drive system and also optimising nebulisation.

The nebulisation control circuit comprises block B which is a pulse width modulation to voltage convertor; block C is a voltage controlled oscillator; block D is the main drive circuitry comprising, inter alia, field effect transistors; block E which is a matching circuit comprising a step-up transformer; and block F is a current feedback device. The system further comprises: block M which is a pulse width modulation unit which drives fan motor N connected to fan 58; membrane keyboard component G is control panel 34; audible and visual display system L which is also partly formed by control panel 34; communications port K for retrieving data from micro-processor and reprogramming the micro-processor A; non-volatile memory component H; drive circuitry temperature monitor component I and transducer crystal temperature monitor component J.

Generally, the nebuliser is designed to efficiently produce a fine mist from a liquid drug situated on the ultrasonic crystal 62 at the bottom of the nebulisation chamber 50*c*. The nebulisation rate is controlled from the membrane keyboard G and on completion of the therapy, when the drug has substantially run out, the unit will automatically turn itself off. Completion is indicated by the illumination of LED 38 and by the emission of an audible beep from a buzzer, these aspects are generally represented by the component L in FIG. 12. The user varies parameters using membrane keyboard G which information is input into microprocessor A to control the rate of nebulisation and the various outputs at component L.

Referring to FIG. 13 there is shown a circuit diagram of a preferred embodiment of the control circuitry for the nebuliser 10. There are shown various ports JP1 to JP6 which are used as follows. JP1 is the output port to the fan drive system M which is connected to the fan motor N which in turn is connected to fan 58. JP2 is the output port to the crystal driving circuit D which is connected to piezo-electric crystal 62. Transformer T1 and the crystal 62 form the matching circuit E shown in block diagram 12. JP3 is a dc voltage input port such as that represented by socket 23 in FIG. 1. JP4 is the user control input connected to keyboard membrane G. JP5 is the programmers communication port K which is also represented by the numeral 42 in FIG. 3 for example. JP6 is the connection to the temperature control thermistor situated underneath the transducer crystal; it therefore forms part of crystal temperature monitor component J.

The electrical circuitry drives the piezo-electric crystal 62 at a high voltage and high frequency. The frequency is selected so that it is at or near the anti-resonance frequency of the transducer and also to produce a controlled mist having an optimum particle size for the specific intended use of the nebuliser.

Referring to FIG. 11 there is shown a characteristic impedance versus frequency curve for a piezo-electric crystal where the resonant condition of minimum impedance is indicated at a frequency R. The maximum impedance or anti-resonant frequency is indicated by the letters AR. It is known to operate in the minimum impedance regime which might typically be of the order of 1.3 MHz, however, the system described here operates at or near the impedance maximum which is in the region of the anti-resonant frequency which might, for example, be of the order of 1.46 MHz. FIG. 11 shows that the impedance at the minimum is about 3 ohms whilst at the maximum it is about 1000 ohms. It is found that the impedance properties of a piezo-electric crystal can be varied for example by varying the capacitance of the crystal assembly by changing the size of the electrical contacts such as the diameter of contact 65.

The electronic circuitry is powered by a 12 volt dc input applied to connector JP3. Unit 12 shown in FIG. 1 therefore may comprise a 240 volt to 12 volt transformer and full wave rectification device in order to supply a 12 volt dc signal to socket 23 of hand-held unit 14. The input at JP3 is filtered for high frequency rejection by common mode choke F1 and capacitors C18 and C19. A 5 V regulated supply Vcc to power the micro-controller A and logic circuitry is provided by regulator U2.

The selection of frequency depends on the intended use of the transducer. For treatment of asthma it is found that a particle size of 3 to 5 micrometers is useful in providing adequate drug particle absorption and retention in a patients lungs. For antibiotic treatment an average particle size less than 2 micrometers is found to be effacatious. The range of an average particle size generated by ultrasonic nebulisers is known to depend on several factors including frequency of oscillation of the transducer. It is found that an operating frequency in the range of 1.36 to 1.56 MHz and more specifically 1.46 MHz, produces a good distribution of particle sizes for the treatment of asthma. The specific crystal used in the transducer 60 is therefore selected to have an anti-resonant frequency in this range for this application.

The nebuliser 10 is operated by the user by means of membrane keypad G connected at JP4. The keyboard comprises four switches which have the following effect; the "on" switch starts nebulisation by enabling the output to the ultrasonic crystal. Pressing the "on" button is annunciated by a short beep from the piezo-electric buzzer Y1 (of component L). The green "on" LED 36 is also illuminated and remains on until the nebulisation chamber becomes empty or the hand set is turned off; the "off" switch stops nebulisation and inhibits the fan (if nebulisation is in progress) and turns the hand set off, the LED's 36 and 38 are extinguished and electronic circuitry becomes inactive. An audible beep is emitted by piezo-electric buzzer Y1. The "off" switch does not isolate the supply voltage and power still remains to the circuitry. The increase or "up" switch increases the rate at which the nebulisation occurs by increasing the power supply to the ultrasonic crystal by increasing the "on" period to the "off" period of the voltage applied to the crystal. These values are retained in the non-volatile memory and is used when the nebuliser is next used to retain the same setting. Associated with an increase in nebulisation is an increase in fan speed. The decrease or "down" switch decreases the rate at which the nebulisation occurs by reducing the power supply to the ultrasonic crystal by reducing the on period in relation to the off period of voltage applied to the crystal. Associated with a decrease in nebulisation is a decrease in fan speed.

The micro-processor A is, for example, a National Semiconductor COP888CF 8 bit single chip micro-controller. This controls all the functions of the circuit other than those just described which are input by the user. The micro-processor used here is a 44 pin device and table 1 shows the name given to each of these together with a brief description of its functions. The micro-controller A includes analogue to digital converters, for example, for converting the analogue signals from the temperature thermistors RT1 and that connected at JP6, and the current amplifier output from component F.

The basic drive process to oscillate the transducer crystal 62 in order to nebulise the medicament is controlled primarily by two outputs from micro-processor A at pins 25 and 28. A pulse width modulated binary output from pin 25 of micro-controller A is filtered by resistor R5 and capacitor C2 to produce a variable DC voltage at pin 9 of voltage controlled oscillator U1 (block component C) dependent on the pulse sequence from micro-controller A. The voltage controlled oscillator used in this example is a 74HC4046 device. The continuous frequency output from U1 is generated at pin 4, VC out. The frequency depends on the voltage at pin 9 of U1 and this is controlled by varying the mark space ratio of the pulse width modulated output from micro-controller A at pin 25. The period of the pulse width modulated mark space is 0.38 micro-seconds and the mark space ratio is limited to prevent the filtered voltage at the output of block diagram component B exceeding the range of 1 to 4 volts. Naturally, the selection of components for pulse width modulation to voltage device B can be varied to suit different pulse width modulational mark space periods and ratios, and to suit the type of voltage controlled oscillator in order to generate a variety of frequency outputs.

The continuous frequency output generated by voltage frequency convertor U1 (block diagram component C) is fed to input 3 of the output driver (block diagram component D) component U4A at pin 3. Component U4A in this specific example is a 74HC74"D" type latch. The frequency input at pin 3 is divided by two to provide an even complimentary output at pins 6 and 5 of component U4A. The output at pins 6 and 5 are further controlled by the micro-controller A at pins 4 and 1. Pin 28 of micro-controller A provides an output signal which controls the period of on and off states of latch U4A. The output from pins 6 and 5 of latch U4A are fed to inputs 2 and 4 of component U6. The mark/space period of enable/disable pulse from pin 28 of micro-controller A is set to about 0.3s and latch U4A is enabled and disabled for varying ratios within this period according to the power requirement to drive the transducer. U6 may, for example, be a TSC426COA device which increases the drive voltage from plus 5 volts to plus 12 volts and increases the output current drive capability to drive the field effect transistors Q1 and Q2. The power FET's work in push pull to drive the step-up transformer T1 to produce a drive voltage across the crystal 62 of around 100 V rms.

It is found that transformer T1 is preferably of a toroidal type which is matched at the ultrasonic vibration frequency of the transducer crystal 62. This step-up transformer and matching circuit arrangement is found to give an efficient power transfer between driver circuit D and the ultrasonic crystal 62.

The transformer is used as a matching network to the transducer. The turns ratio is chosen to produce the correct voltage across the crystal to produce the required amount of nebulisation. The number of turns chosen is such that the transformer inductance and the capacitance of the transducer form a matching circuit at the point of anti-resonance of the transducer when there is no medication in the chamber.

When the medication is added to the chamber the equivalent capacitance of the transducer is increased, such that the apparent anti-resonant point has shifted down approximately 10 KHz. (The micro-controller continues to search for this apparent anti-resonant point to maintain minimum current). However, the crystal sees this as a shift down in frequency on the frequency/impedance graph. A shift off the natural anti-resonant point of the crystal as shown in FIG. 11 results in lowering of impedance. Hence the circuit will see an increase in current with medication in the chamber and a decrease without medication.

In a preferred form the transformer consists of a toroidal ring of carbonyl iron measuring 12.7 mm in outer diameter and 7.62 mm inner diameter with a depth of 4.75 mm.

Other parameters are as follows:

1) Initial permeability=25/–3

Inductance factor=12.4 (max) 9.72 (min)

Maximum working temperature=150'c

The primary may be formed from two coils each consisting of 6 turns of 0.56 mm diameter wire, whilst the secondary may be an 85 turn coil of 0.25 mm diameter wire.

Of course, the matching circuit could be used in other nebulisers independent of the feature of minimum current seeking. The current through the output circuit driving the transducer crystal passes through resistor R13 which is part of current amplifier device F. The voltage across resistor R13 is filtered by resistor R9 and capacitor C6 to provide a smooth voltage input to operational amplifier U5A at pin 3. For example, amplifier USA may be a LM358 device. The amplified voltage is input to micro-controller A at pin 10. Pin 10 is an analogue to digital convertor and the programmed micro-controller A monitors the input at pin 10 in order to monitor the crystal driver current. A method of scanning through the operational frequency is used to minimise the current drawn by the driver circuitry.

Micro-controller A is programmed to operate driver circuit D at a frequency corresponding to the anti-resonant frequency of the ultra-sonic crystal 62. This frequency is determined by searching for the minimum current drawn by the output circuitry which, as previously stated, is passed through resistor R13. The input voltage at pin 10 is sampled every 0.3 seconds after which micro-controller A shifts the frequency as set amount. For example, a total resolution of 128 steps may be produced in the range of voltage outputs from PWM to voltage convertor B and thus the range of posible frequencies from volge control oscillator C. As alreasdy stated a reasonable range from anti-resonant to resonance of a transducer crystal used in this system is of the order of 0.15 MHz. It may therefore be useful to be able to scan a range of about 0.3 MHz. Accordingly, the output from micro-controller A is incremented by varying the mark/space ratio of the output signal from pin 25 to pulse width to voltage device B within the set mark/space period previously described. Alternatively, smaller ranges of frequencies may be scanned and by a differing amount of resolution, e.g. fewer of greater increment divisions in the scan range. The frequency of a given crystal anti-resonance varies with temperatures, for example, the frequency might decrease by 8 KHz between 25° C. and 85° C. Such properties need to be accounted for in the scan parameters of the nebuliser.

Having incremented the frequency by one division out of its total range of resolution say 128 increments, in either direction the input at micro-controller pin 10 is again monitored to determine whether the current drawn by the driver circuit D is greater or lower than the previous amount. If the current is less then the micro-controller A is programmed to continue the search in that the same direction and therefore increments the frequency by a further step in that direction. This process continues until the current increases and at that point the micro-controller reverses the direction of frequency incrementation. This process of scanning the crystal driver circuitry and therefore frequency of operation is continuous. However, incrementally, say every 10 samples, the micro-controller increases and/or decreases the frequency incrementation by a larger value, say 10 increments, in order to obtain a single sample. If the current drawn at the large incremental scan frequency is larger then the micro-controller returns to operation at the previous frequency.

The input at pin 10 is stored in non-volatile memory component U7 (block diagram component H), in order to then be able to compare this value with the value obtained at the large incremental scan frequency. This technique of jumping out of the routine scan process enables the micro-processor A to search for a true minimum in the drive current which might otherwise be determined by background noise or other local smaller current minima. The system thereby avoids operating at an incorrect frequency in terms of power optimisation.

Micro-controller A also switches off the nebulisation process completely when the nebulisation chamber 50*c* becomes empty of liquid L. This is sensed by a dramatic change in the current drawn by driver circuit D. In this specific example it is found that when the liquid runs out the current drawn by driver circuit D decreases sharply. When the crystal is being driven with a drug in situ above it, the micro-controller measures the current and constantly compares this value with a reference value held in non-volatile memory H. The difference between the present and stored reference value is calculated in order to determine when and if this value is greater than a stored difference value it is assumed that the liquid drug has been fully used and liquid nebulisation has stopped. The stored current value is the average current used in the previous use of the nebuliser. The difference value is also held in the non-volatile memory but is programmed at the initial set-up. At the end of each session of treatment the average current is updated into the non-volatile memory H to be used as the reference value during the next usage of the nebuliser.

Whatever the instantaneous operational frequency of the ultrasonic crystal, the power output to the ultrasonic crystal is controlled by the micro-processor A by varying the on-time and off-time as previously described. The signal is sent from pin 28 of micro-processor A to component U4A of drive circuit D. If the user presses the increase button 39 of keyboard membrane G then the pulse on time is increased. The present settings for the on-period and off-period are stored in memory to retain the settings in use. Similarly, pressing decrease button 40 causes the on pulse width to decrease.

Micro-processor A further controls the motor fan speed by pulse width modulation. The drive frequency being kept constant. The fan speed is changed in line with the increases and decreases in power supplied to the ultrasonic crystal is controlled by the user operating the membrane keyboard increase and decrease switches 39 and 40. Thus, depressing the decrease button 40 of keyboard membrane G not only decreases the power to the ultrasonic crystal but also decreases the fan speed by reducing the on time of its pulse width modulated drive signal; similarly, pressing the increase button increases both power to the crystal and increase on time to the fan motor.

The nebuliser comprises various audible and visual displays which provide information to the user as previously described. These generally are represented by block diagram component L which comprises green "on" LED36 and "Liquid empty" red LED38. There is further provided a piezo buzzer Y1 which provides the various audible signals, for example, when turning the nebuliser on using button 35 or when the therapeutic drug runs out.

The system further comprises two temperature feed-back systems I and J. Micro-processor A monitors the temperature at the transducer 60 using a thermistor placed beneath the transducer crystal 62. The thermistor is connected to port JP6 of block diagram component J. The analogue output of component J is fed to pin 11 of micro-processor A and this is monitored against a temperature threshold value held in non-volatile memory H. If the threshold value is exceeded on time then the pulse width to the ultrasonic crystal is reduced thereby reducing the power dissipated in the ultrasonic crystal 62. The fan speed however remains unchanged to aid cooling. If the temperature remains above the threshold for a preset time then the power to the crystal is reduced by a further increment. This process continues until the temperature drops below the threshold value or reaches the minimum power value. The preset time constant is held in the non-volatile memory H. Similarly a thermistor RT1 is placed on the printed circuit board between power FET's Q1 and Q2, or otherwise adjacent to them, and is used to determine the temperature in the driver circuit D. Whilst thermistors are used here other temperature sensitive devices could be used. The output from driver circuit temperature monitor I is input pin 9 of micro-processor A. If the input to micro-processor A exceeds a threshold value held in non-volatile memory H then the power output to drive circuit D is reduced incrementally in the same manner described for the ultrasonic crystal temperature control process. Again, the fan speed is not changed in order to aid cooling.

Throughout the operation the micro-processor A saves various values in non-volatile memory H. Component U7 of block diagram component H can for example be an electrical erasable programmable memory (EEPROM) such as a 93C06 device. This particular device has facility to store 256 bits of data. There is further provided a communication port K which might typically be a serial RS232 connector. Access to the communication port is provided in the front panel of the hand-held device 14. The port itself is normally covered by a small plastic insert to protect it from the ingress of dirt. The communication port is connected directly to microcontroller A pins 1 and 2 which are output and input data lines respectively. The two way communication to the micro-controller A allows diagnostic analysis of the system. Thus temperature frequency current consumption and the number of lines respectively. The two way communication to the micro-controller A allows diagnostic analysis of the system. Thus temperature frequency current consumption and the number of times the nebuliser unit 14 has been used can be determined by accessing the micro-controller using communications port K. Various identifying codes can also be stored such as serial number, model number and hardware version used in the device. The programme operating microprocessor A can also be structured to allow the following: variation of the time before nebulation is stopped after an empty chamber is detected; variation of the ultrasonic crystal temperature threshold; variation of the transistor temperature threshold; variation of the temperature time constant i.e. time before reducing output power a further increment; variation of the time delay after start up of nebulisation before an average current is read. The communication port also allows manual control by a programmer over individual parameters such as frequency output power and motor speed. This is useful in order to facilitate testing of nebuliser 10.

TABLE 1

| PIN NUMBER | NAME | DESCRIPTION |
|---|---|---|
| 1 | C2 | Communication - output |
| 2 | C3 | Communication - input |
| 3 | G4 | Data I/P - eeprom memory |
| 4 | G5 | Serial clock - eeprom memory |
| 5 | G6 | Data out - eeprom memory |
| 6 | G7 | Clock Resonator - output |
| 7 | CXI | Clock Resonator - input |
| 8 | Vcc | +5 volt supply |
| 9 | I0 | TH1 Thermistor input (transistor) |
| 10 | I1 | Output from current amplifier |
| 11 | I2 | TH2 Thermistor input (crystal) |
| 12 | I3 | — |
| 13 | I4 | — |
| 14 | I5 | Mode - version sense |
| 15 | I6 | — |
| 16 | I7 | — |
| 17 | Agnd | Analogue Ground |
| 18 | Vref | Voltage Reference input |
| 19 | L2 | Membrane key input 'OFF' |
| 20 | L3 | Membrane key input 'ON' |
| 21 | C4 | Membrane key input 'INCREASE' |
| 22 | C5 | Membrane key input 'DECREASE' |
| 23 | C6 | — |
| 24 | C7 | — |
| 25 | L4 | PWM OUTPUT-FREQUENCY CONTROL |
| 26 | L5 | VOLTAGE CONTROLLED OSC. INHIBIT |
| 27 | L6 | PWM OUTPUT-MOTOR CONTROL |
| 28 | L7 | DRIVER CIRCUIT ENABLE |
| 29 | D0 | — |
| 30 | D1 | — |
| 31 | D2 | — |
| 32 | D3 | — |
| 33 | D4 | — |
| 34 | D5 | VISUAL GREEN L.E.D. 'ON' |
| 35 | D6 | AUDIBLE BUZZER ENABLE |
| 36 | D7 | VISUAL RED L.E.D. 'EMPTY' |
| 37 | GND | GROUND |
| 38 | RESET | POWER LINE RESET |
| 39 | G0 | — |
| 40 | G1 | WATCHDOG OUTPUT |
| 41 | G2 | — |
| 42 | G3 | — |
| 43 | C0 | CHIP SELECT EEPROM |
| 44 | C1 | — |

We claim:

1. A nebuliser, comprising:

an electrically-energisable ultrasonic transducer in the form of a piezo-electric crystal;

a transducer drive system; and a high-frequency drive signal generated by the drive system for energising the transducer, the transducer being connected to the drive signal to receive said drive signal and the transducer, when energised by the drive signal, being operative to cause physical vibrations in a fluid to be nebulised, the transducer having a frequency-dependent impedance characteristic exhibiting a maximum impedance at an anti-resonance frequency corresponding to an anti-resonance condition of the crystal, the drive system further comprising frequency control means operable to adjust the frequency of the drive signal so as to be maintained substantially equal to the anti-resonance frequency.

2. A nebuliser according to claim 1, wherein said drive system comprises:

means for varying the power supplied by the drive signal to the transducer in dependance on user input by turning on and off the drive signal and varying the on and off periods during which the drive signal is turned on and off.

3. A nebuliser according to claim 1, wherein said drive system comprises:

means for automatically controlling the frequency of said drive signal, the frequency control means comprising:
means for modulating pulse width for generating a binary pulse sequence of variable mark/space ratio;
means for converting the binary pulse sequence into a voltage, the magnitude of the voltage dependent on said mark/space ratio; and
a voltage controlled oscillator connected to the convertor means to receive the voltage produced by the convertor means, the oscillator being operative to produce an output signal of a frequency dependent on said voltage; and means for driving a circuit connected to the oscillator to receive said output signal, the circuit drive means being operative to produce said drive signal dependent on said output signal, the mark/space ratio of said binary pulse sequence being controlled by said pulse width modulation means such that the frequency of the drive signal causes the transducer to operate in said region of elevated impedance.

4. A nebuliser according to claim 1, wherein said drive system comprises:

means for automatically controlling the frequency of said drive signal, the frequency control means comprising:
means for modulating pulse width for generating a binary pulse sequence of variable mark/space ratio;
means for converting the binary pulse sequence into a voltage, the magnitude of the voltage dependent on said mark/space ratio; and
a voltage controlled oscillator connected to the convertor means to receive the voltage produced by the convertor means, the oscillator being operative to produce an output signal of a frequency dependent on said voltage; and means for driving a circuit connected to the oscillator to receive said output signal, the circuit drive means being operative to produce said drive signal dependent on said output signal, the mark/space ratio of said binary pulse sequence being controlled by said pulse width modulation means such that the frequency of the drive signal causes the transducer to operate in said region of elevated impedance; and means for controlling the power supplied by the drive signal to the transducer in dependence on user input, wherein the power control means comprises means for setting the on/off time of the drive signal forming part of said circuit drive means.

5. A nebuliser according to claim 1, wherein the frequency control means further comprises means for sensing the transducer drive current, the frequency control means for being operative to adjust the frequency of the drive signal such as to minimise said drive current.

6. A nebuliser according to claim 5, wherein the frequency control means searches for the minimum transducer drive current by periodically modifying the frequency of the drive signal and determining whether the resultant drive current is greater or less than the previous transducer drive current value.

7. A nebuliser as claimed in claim 1, wherein the transducer further comprises:

two electrical contacts secured to the crystal having opposite electrical polarities; and a shim layer attached to the upper surface of the crystal, the shim layer in direct contact with the fluid to be nebulised.

8. A nebuliser as claimed in claim 1, further comprising a nebulising chamber, wherein the transducer is placed in a recess in the bottom of the nebulising chamber and held in position using a seal and a clamp which are placed in contact with said transducer.

* * * * *

UNITED STATES PATENT AND TRADEMARK OFFICE
CERTIFICATE OF CORRECTION

PATENT NO.   : 5,551,416
DATED        : September 3, 1996
INVENTOR(S)  : Stimpson et al.

It is certified that error appears in the above-indentified patent and that said Letters Patent is hereby corrected as shown below:

At column 4, line 34, delete the second occurrence of "and" and insert therefor --in--.

At column 7, line 28, delete "effacatious" and insert therefor --efficacious--.

At column 9, line 14, insert --2)-- before "Inductance".

At column 9, line 15, insert --3)-- before "Maximum".

At column 9, line 15, delete "'c" and insert therefor --°C--.

At column 9, line 40, delete "as" and insert therefor --a--.

At column 9, line 43, delete "volge" and insert therefor --voltage--.

At column 9, line 44, delete "alreasdy" and insert therefor --already--.

At column 9, line 53, delete "of" and insert therefor --or--.

At column 10, line 54, after "crystal", insert --which--.

At column 10, line 62, delete "increase" and insert therefor --increases--.

At column 11, lines 48-51, delete "lines respectively. The two way communication to the micro-controller A allows diagnostic analysis of the system. Thus temperature frequency current consumption and the number of".

At column 11, line 57, delete "nebulation" and insert therefor --nebulisation--.

UNITED STATES PATENT AND TRADEMARK OFFICE
CERTIFICATE OF CORRECTION

PATENT NO. : 5,551,416
DATED : September 3, 1996
INVENTOR(S) : Stimpson et al.

It is certified that error appears in the above-indentified patent and that said Letters Patent is hereby corrected as shown below:

At column 12, line 51, delete "signal" and insert therefor --system--. At column 14, line 17, delete "for".

Signed and Sealed this

Eleventh Day of November, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,551,416

DATED : September 3, 1996

INVENTOR(S) : Stimpson et al.

It is certified that error appears in the above-identified patent and that said Letters Patent is hereby corrected as shown below:

At column 4, line 34, delete the first occurrence of "and" and insert therefor --in--.

At column 7, line 28, delete "effacatious" and insert therefor --efficacious--.

At column 9, line 14, insert --2)-- before "Inductance".

At column 9, line 15, insert --3)-- before "Maximum".

At column 9, line 15, delete "°c" and insert therefor --°C--.

At column 9, line 40, delete "as" and insert therefor --a--.

At column 9, line 43, delete "volge" and insert therefor --voltage--.

At column 9, line 44, delete "alreasdy" and insert therefor --already--.

At column 9, line 53, delete "of" and insert therefor --or--.

At column 10, line 54, after "crystal", insert --which--.

At column 10, line 62, delete "increase" and insert therefor --increases--.

At column 11, lines 48-51, delete "lines respectively. The two way communication to the micro-controller A allows diagnostic analysis of the system. Thus temperature frequency current consumption and the number of".

At column 11, line 57, delete "nebulation" and insert therefor --nebulisation--.

UNITED STATES PATENT AND TRADEMARK OFFICE
CERTIFICATE OF CORRECTION

PATENT NO. : 5,551,416
DATED : September 3, 1996
INVENTOR(S) : Stimpson et al.

It is certified that error appears in the above-identified patent and that said Letters Patent is hereby corrected as shown below:

At column 12, line 51, delete "signal" and insert therefor --system--. At column 14, line 17, delete "for".

At column 14, line 39, insert the following claims:

9. A nebuliser according to claim 5, further comprising means for comparing the transducer drive current with a predetermined threshold value and for generating a termination signal when the drive current falls below the threshold value indicating the fluid has been completely nebulised, the drive system being turned off in response to the termination signal.

10. A nebuliser according to claim 9, wherein the threshold value comprises the sum of a variable usage reference value and a predetermined difference value, the comparing means deriving an operational difference value by determining the difference between the usage reference value and the drive current, the comparing means thereafter comparing the operational difference value with the predetermined difference value and providing the termination signal when the drive current falls below the threshold value and the operational difference value exceeds the predetermined difference value.

11. A nebuliser according to claim 10, wherein the usage reference value is determined by the drive system based on the drive current during a previous session of use of the nebuliser,

UNITED STATES PATENT AND TRADEMARK OFFICE
CERTIFICATE OF CORRECTION

PATENT : 5,551,416

DATED : September 3, 1996

INVENTOR(S): Stimpson et al.

It is certified that error appears in the above-identified patent and that said Letters Patent is hereby corrected as shown below:

12. A nebuliser according to claim 10, wherein the predetermined reference value is fixed.

13. A nebuliser according to claim 1, further comprising a nebulising chamber having a bottom for holding the fluid in physical contact with the transducer, an outlet in fluid communication with the nebulising chamber, and an air flow passage which passes through said nebulising chamber to draw off nebulised fluid to an outlet.

14. A nebuliser according to claim 13, wherein the outlet is adapted to fit directly into the mouth or nasal orifice of a user, the outlet comprising an exhaust outlet for directing exhaled gases away from the user.

15. A nebuliser according to claim 14, wherein the exhaust outlet directs the exhaled gases in a direction generally opposite to the direction of nebulised fluid passing through the outlet to the user.

UNITED STATES PATENT AND TRADEMARK OFFICE
CERTIFICATE OF CORRECTION

PATENT NO. : 5,551,416

DATED : September 3, 1996

INVENTOR(S) : Stimpson et al.

It is certified that error appears in the above-identified patent and that said Letters Patent is hereby corrected as shown below:

16. A nebuliser according to claim 13, wherein the transducer is placed in a recess in the bottom of the nebulising chamber and held in position using a seal and a clamp which are placed in contact with the transducer.

17. A nebuliser according to claim 8, wherein the clamp is thermally conductive and acts as a heat sink to the transducer.

18. A nebuliser according to claim 1, wherein the transducer drive system comprises a step-up transformer comprising primary and secondary coils, the secondary coil connected to the transducer.

19. A nebuliser according to claim 18, wherein the transformer inductance and the capacitance of the transducer form a matching circuit at a frequency corresponding substantially to the anti-resonance frequency of the transducer when there is no fluid in the chamber.

20. A nebuliser according to claim 18, wherein the transformer is a toroidal type.

UNITED STATES PATENT AND TRADEMARK OFFICE
CERTIFICATE OF CORRECTION

PATENT NO. : 5,551,416

DATED : September 3, 1996

INVENTOR(S) : Stimpson et al.

It is certified that error appears in the above-identified patent and that said Letters Patent is hereby corrected as shown below:

21. A nebuliser according to claim 20, wherein the toroidal type transformer comprises a ferrous core made from carbonyl iron.

This certificate supercedes Certificate of Correction issued November 11, 1997.

Signed and Sealed this

Third Day of August, 1999

*Attest:*

Q. TODD DICKINSON

*Attesting Officer*  Acting Commissioner of Patents and Trademarks